(12) United States Patent
Inoue et al.

(10) Patent No.: US 9,480,536 B2
(45) Date of Patent: Nov. 1, 2016

(54) SURGERY ASSISTANCE DEVICE

(71) Applicant: OLYMPUS CORPORATION, Tokyo (JP)

(72) Inventors: Shintaro Inoue, Asaka (JP); Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/569,871

(22) Filed: Dec. 15, 2014

(65) Prior Publication Data

US 2015/0100069 A1 Apr. 9, 2015

Related U.S. Application Data

(63) Continuation of application No. PCT/JP2013/067536, filed on Jun. 26, 2013.

(30) Foreign Application Priority Data

Jul. 3, 2012 (JP) .................................. 2012-149341

(51) Int. Cl.
*A61B 17/94* (2006.01)
*B25J 9/16* (2006.01)
(Continued)

(52) U.S. Cl.
CPC .............. *A61B 90/50* (2016.02); *A61B 34/30* (2016.02); *A61B 34/37* (2016.02); *A61B 2034/2065* (2016.02); *A61B 2034/301* (2016.02); *A61B 2090/061* (2016.02); *A61B 2090/067* (2016.02)

(58) Field of Classification Search
CPC .................. A61B 17/00234; A61B 2017/003; A61B 2017/0034; A61B 2019/2203; A61B 2017/2207; A61B 2019/2223; A61B 2019/223; A61B 2019/2249; A61B 2019/5251; A61B 2019/5265; A61B 2019/5255; A61B 2019/5259; A61B 1/00193; A61B 2017/00207; A61B 2019/5227; A61B 2019/2273; B25J 9/1689; B25J 9/02; G06F 3/014; G06F 3/0325; G06K 2009/3225; G06K 9/00624; G06K 9/3216; G05B 2219/36418; G05B 2219/40557
See application file for complete search history.

(56) References Cited

U.S. PATENT DOCUMENTS

2005/0075739 A1* 4/2005 Nishizawa ............. B25J 9/1065
700/65
2007/0287992 A1 12/2007 Diolaiti et al.
(Continued)

FOREIGN PATENT DOCUMENTS

JP 2002-287613 A 10/2002
JP 2005-103741 A 4/2005
(Continued)

OTHER PUBLICATIONS

International Search Report dated Sep. 17, 2013 issued in PCT/JP2013/067536.
(Continued)

*Primary Examiner* — Dale Moyer
(74) *Attorney, Agent, or Firm* — Scully, Scott, Murphy & Presser, PC

(57) ABSTRACT

A surgery assistance device includes an operation input section, a motion section which is formed with a channel into which a surgical instrument is insertable and is capable of moving through the channel, a movement amount detection means detecting a treatment section movement amount, a motion section information calculation means calculating motion section information, and a motion control unit controlling motion in the motion section based on a manipulation order.

9 Claims, 10 Drawing Sheets

(51) Int. Cl.
*B25J 3/00* (2006.01)
*A61B 19/00* (2006.01)

(56) References Cited

U.S. PATENT DOCUMENTS

| | | | | |
|---|---|---|---|---|
| 2009/0198104 A1* | 8/2009 | Sugiyama | ........... | A61B 1/00039 600/146 |
| 2010/0256960 A1 | 10/2010 | Ortmaier et al. | | |
| 2011/0118752 A1* | 5/2011 | Itkowitz | ............. | A61B 19/2203 606/130 |
| 2011/0118753 A1* | 5/2011 | Itkowitz | ............. | A61B 19/2203 606/130 |
| 2012/0071891 A1* | 3/2012 | Itkowitz | ............. | A61B 19/2203 606/130 |
| 2012/0071892 A1* | 3/2012 | Itkowitz | ............. | A61B 19/2203 606/130 |
| 2012/0221145 A1* | 8/2012 | Ogawa | ....................... | B25J 3/04 700/259 |
| 2013/0024024 A1* | 1/2013 | Namiki | ............. | A61B 1/00149 700/245 |
| 2014/0148820 A1* | 5/2014 | Ogawa | ................... | A61B 17/29 606/130 |
| 2014/0303643 A1* | 10/2014 | Ha et al. | ............ | A61B 19/2203 606/130 |
| 2015/0073436 A1* | 3/2015 | Inoue | ..................... | A61B 19/22 606/130 |
| 2015/0327940 A1* | 11/2015 | Inoue | ................. | A61B 19/2203 606/130 |

FOREIGN PATENT DOCUMENTS

| | | |
|---|---|---|
| JP | 2008-212349 A | 9/2008 |
| JP | 2009-178416 A | 8/2009 |
| JP | 4672031 B2 | 4/2011 |
| JP | 2011-194163 A | 10/2011 |
| WO | WO 2012/044334 A2 | 4/2012 |

OTHER PUBLICATIONS

Extended Supplementary European Search Report dated Mar. 4, 2016 in related European Application No. 13 81 3012.5.

* cited by examiner

SURGERY ASSISTANCE DEVICE

This application is a continuation application based on PCT Patent Application No. PCT/JP2013/067536, filed Jun. 26, 2013, claiming priority based on Japanese Patent Application No. 2012-149341, filed Jul. 3, 2012, the content of which is incorporated herein by reference.

FIELD OF THE INVENTION

The present invention relates to a surgery assistance device.

DESCRIPTION OF RELATED ART

Conventionally, a variety of surgery assistance devices are considered for performing a procedure by remote control. For example, Japanese Patent No. 4672031 discloses a surgery assistance device.

In the surgery assistance device of Japanese Patent No. 4672031, signals are transmitted from a joystick (operation input section) by operating of the joystick and an active bending section provided in an insertion section (motion section) of an electronic endoscope is bent based on the signals.

The insertion section is formed with a channel into which a flexible treatment tool (surgical instrument) can be inserted.

The surgery assistance device of Japanese Patent No. 4672031 controls a maximum bending speed, which is a maximum value of speed at which the active bending section is bent, to be changed when the active bending section is driven, namely, when the active bending section is bent. Specifically, the surgery assistance device has an insertion mode in which the treatment tool does not protrude from a treatment tool protrusion port (distal end opening) and a treatment mode in which the treatment tool protrudes from the treatment tool protrusion port. The maximum bending speed in the insertion mode is set to twice that of the treatment mode.

Thus, when the insertion section is inserted to a target portion, the insertion mode is set so that the active bending section may be rapidly bent to be rapidly inserted. On the other hand, when the treatment mode is set and the treatment tool protrudes from the treatment tool protrusion port to perform various curative treatments, the speed is easily specified and thus accuracy of the treatment and operability may be improved.

SUMMARY OF THE INVENTION

According to a first aspect of the present invention, a surgery assistance device includes an operation input section configured to output a manipulation order based on input from a user; a motion section which is formed with a channel into which a surgical instrument is insertable and is capable of moving through the channel, the surgical instrument provided with a treatment section at a distal end portion of a flexible surgical instrument insertion section; a movement amount detection means detecting a treatment section movement amount which is at least one of a protrusion length by which the treatment section of the surgical instrument inserted into the channel protrudes forward from a distal end opening of the channel and a rotation angle of the surgical instrument about an axis of the channel; a motion section information calculation means calculating motion section information which is capable of specifying a position and an orientation of the motion section in the distal end opening; and a motion control unit controlling motion in the motion section based on the manipulation order, wherein the operation input section comprises: a detection target object attached to an operation section which operates the treatment section fixed to a proximal end portion of the surgical instrument insertion section; and a detection section detecting the detection target object, wherein the detection section calculates detection target object information capable of specifying a position and orientation of the detection target object, the operation input section outputs the manipulation order based on the detection target object information calculated by the detection section, and the motion control unit controls motion in the motion section based on the detection target object information of the manipulation order, the treatment section movement amount, and the motion section information.

According to a second aspect of the present invention, the surgery assistance device according to the first aspect, the surgery assistance device may further include a fixing means configured to fix a position of the surgical instrument insertion section inserted into the channel with respect to the channel.

According to a third aspect of the present invention, the surgery assistance device according to the first or second aspect, the surgery assistance device may further include a surgical instrument movement section moving the surgical instrument inserted into the channel with respect to the channel.

According to a fourth aspect of the present invention, the surgery assistance device according to any one of the first to third aspects, the detection target object may include a body section attached to the operation section, and a marker provided at the body section. The detection section may calculate the detection target object information using the marker.

According to a fifth aspect of the present invention, the surgery assistance device according to any one of the first to third aspects, the detection target object may include an adaptor attached to the operation section. Furthermore, the detection section may include an articulated arm connected to the adaptor, and a position-orientation detection section detecting a position and orientation of the articulated arm to output the position and orientation as the detection target object information.

According to a sixth aspect of the present invention, the surgery assistance device according to the fourth or fifth aspect, the detection section may calculate the detection target object information by using a coordinate system defining an original point, which is set to have a predetermined positional relation with respect to the operation section, as a reference.

DETAILED DESCRIPTION OF THE PREFERRED EMBODIMENTS (First Embodiment)

Hereinafter, a surgery assistance device according a first embodiment of to the present invention will be described with reference to FIGS. 1 to 9.

Figure 1:
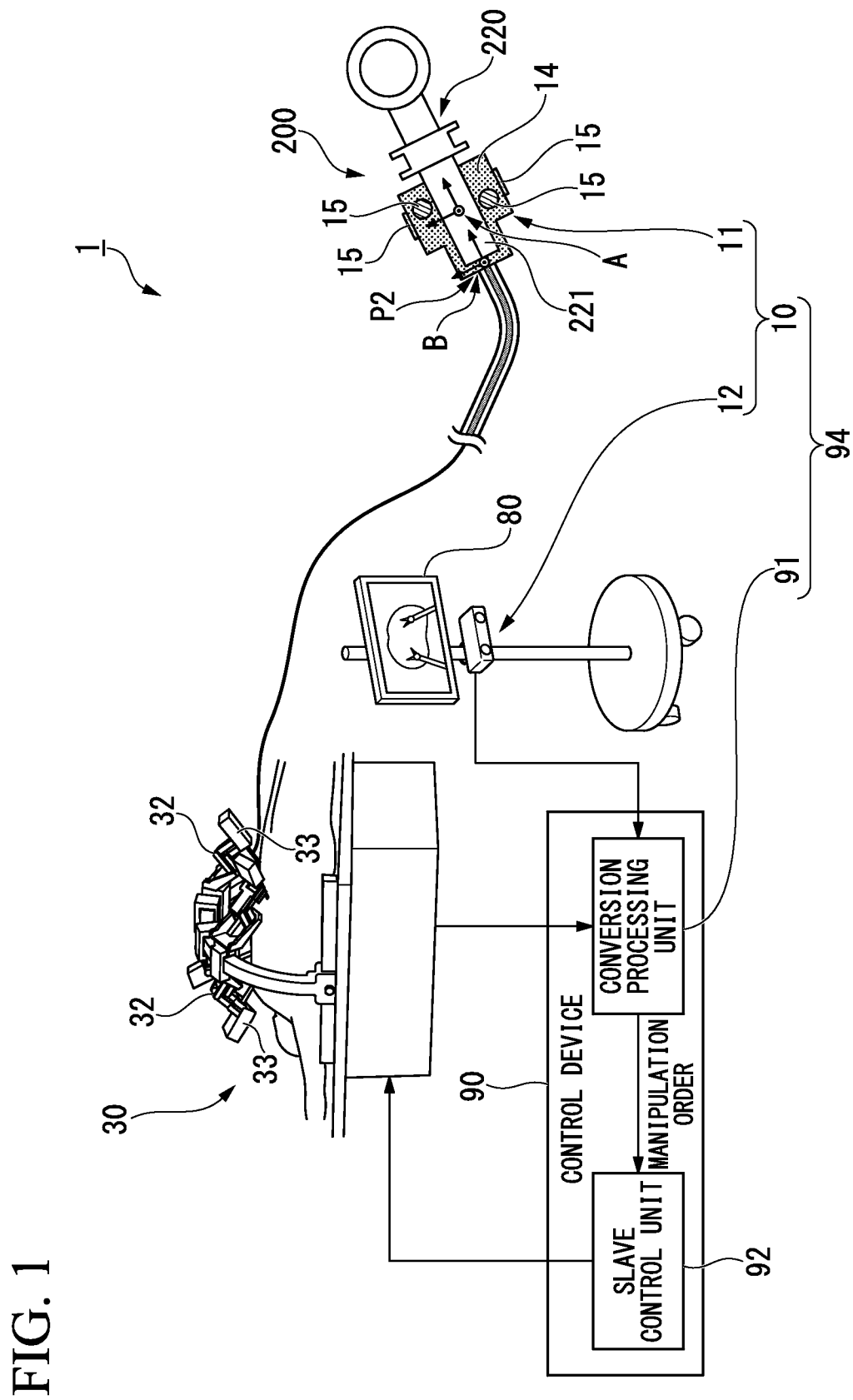
FIG. 1 is a general view showing a configuration of a surgery assistance device according to a first embodiment of the present invention.

As shown in FIG. 1, a surgery assistance device 1 according to the present embodiment includes a master manipulator 10, a slave manipulator (motion section) 30, a display device 80, and a control device 90. The surgery assistance device 1 is configured to be capable of attaching a known flexible treatment tool, as a surgical instrument 200.

Figure 2:
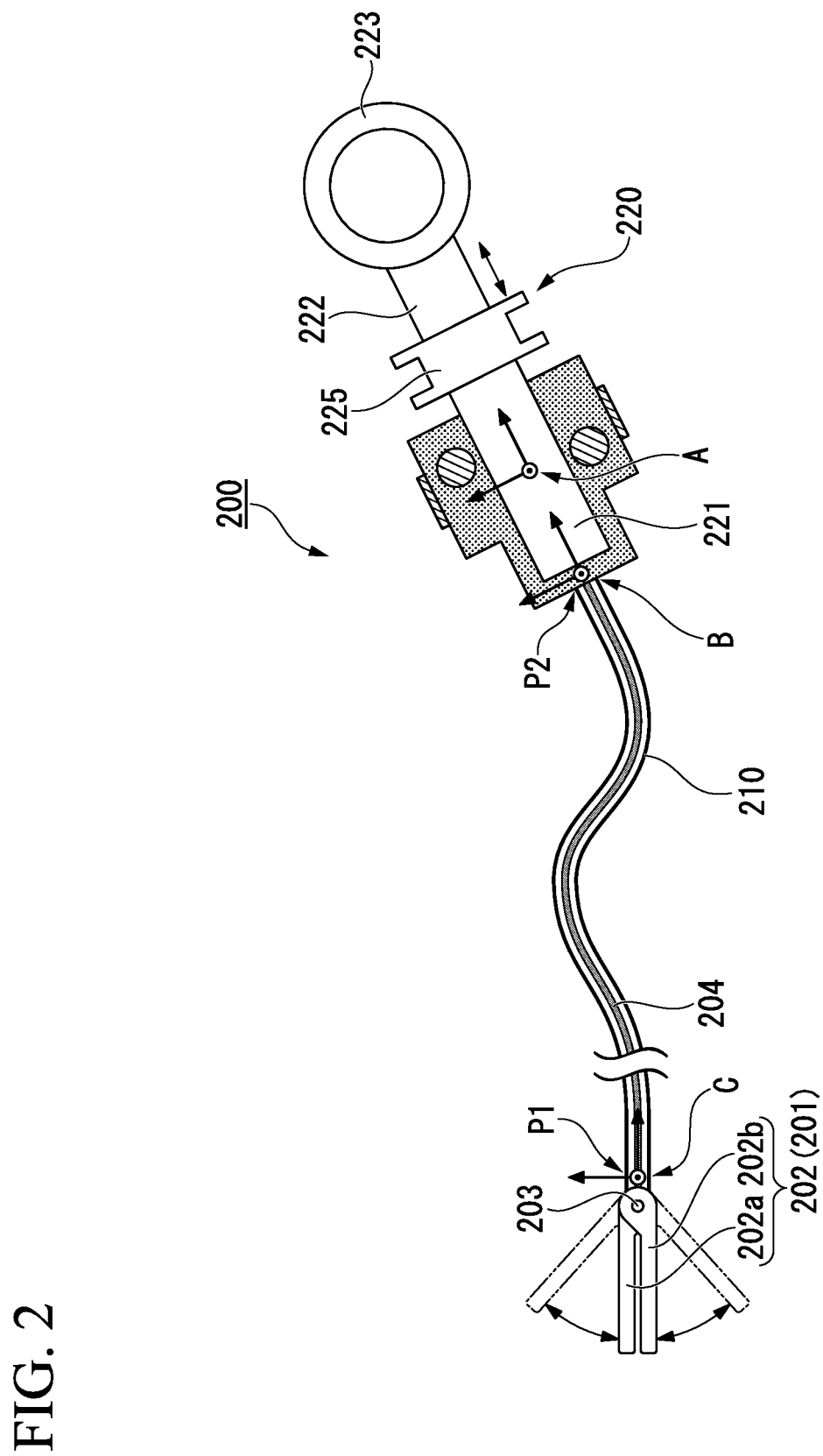
FIG. 2 is a schematic view showing a surgical instrument used with the surgery assistance device according to the first embodiment of the present invention.

The configuration of the surgical instrument 200 is not especially limited. For example, the surgical instrument 200 attached to and used in the surgery assistance device 1 includes a treatment section 201, a surgical instrument insertion section 210, and an operation section 220, as shown in FIG. 2. The treatment section 201 is provided at a distal end portion of the surgical instrument insertion section 210. The operation section 220 is fixed to a proximal end portion of the surgical instrument insertion section 210.

The treatment section 201 may properly select and adopt a known configuration for performing a treatment on biological tissue, such as a forceps, a needle, or a high-frequency knife. In the embodiment, the treatment section 201 is actuated by an operation of the operation section 220. The motion of the treatment section 201 includes, for example, opening and closing of the forceps, protrusion of the needle from the surgical instrument insertion section 210, application of high-frequency current to the high-frequency knife, or the like. Hereinafter, the treatment section 201 will be described using an example in which an openable and closable forceps 202 is provided as the treatment section 201.

The forceps 202 has a pair of forceps pieces 202a and 202b connected by a pin 203 to be rotatable relative to each other. Each of the forceps pieces 202a and 202b is connected to a wire 204 for rotating each forceps piece 202a or 202b about a central axis of the pin 203. A distal end of the wire 204 is connected to the forceps 202. The wire 204 is inserted into the surgical instrument insertion section 210, and connected to the operation section 220.

The surgical instrument insertion section 210 is a flexible cylindrical member. In the embodiment, the configuration of the surgical instrument insertion section 210 is not especially limited so long as the surgical instrument insertion section 210 has a cylindrical shape. For example, the surgical instrument insertion section 210 has a coil sheath around which a metal wire is wound in a coil form, and a covering member which covers the coil sheath. The wire 204 connected to each of the forceps pieces 202a and 202b is inserted into the surgical instrument insertion section 210.

The operation section 220 is fixed to the surgical instrument insertion section 210. Specifically, the operation section 220 includes an operation body 221 and a slider 225. The operation body 221 has a bar shape and the surgical instrument insertion section 210 is fixed to a distal end of the operation body 221. The slider 225 is connected to the operation body 221 and fixed to the wire 204.

The operation body 221 has a rail section 222 which holds the slider 225 such that the slider 225 freely advances and retracts. In addition, the operation body 221 is provided with a finger hooking section 223 for hooking a finger of a user, and the finger hooking section 223 is provided at an end opposite to a side end of the operation body 221 to which the surgical instrument insertion section 210 is fixed.

The slider 225 is a substantially cylindrical member in which a recess for hooking the finger of the user is formed on an outer peripheral surface of the slider 225. By advancing and retracting the slider 225 with respect to the operation body 221, the wire 204 advances and retracts in the surgical instrument insertion section 210.

The master manipulator 10 shown in FIG. 1 is provided to actuate the slave manipulator 30 corresponding to movement of the user. The master manipulator 10 includes a detection target object 11 attached to the surgical instrument 200 and a detection device (detection section) 12 for detecting the detection target object 11. In the embodiment, an operation input section 94 is configured by the master manipulator 10 and a conversion processing unit 91 of the control device 90 to be described later. The operation input section 94 outputs a manipulation order for motion of the slave manipulator 30.

The detection target object 11 is attached at a position at which it does not interfere with the user's grip of the operation section 220 of the surgical instrument 200. For example, in the embodiment, the detection target object 11 is detachably fixed in the vicinity of a connection portion between the operation body 221 and the surgical instrument insertion section 210. The detection target object 11 has a body section 14 attached to the operation section 220 and markers 15 provided on the body section 14.

The body section 14 is a member in which the markers 15 are provided on an outer surface thereof. The markers 15 provided on the body section 14 are provided at three or more positions which are spaced apart from each other on the outer surface of the body section 14. Each of the markers 15 has a predetermined color and shape. For example, in the embodiment, a plurality of markers 15 having the same shape, size, and color, are provided on the body section 14. Each marker 15 is formed on the outer surface of the body section 14, for example, by printing or the like.

The marker 15 is positioned and arranged with respect to the body section 14. For this reason, a position and orientation (direction) of the marker 15 correspond to a position and orientation of the body section 14. Since the body section 14 is fixed to the operation body 221 of the operation section 220, the position and orientation of the marker 15 correspond to a position and orientation of the operation section 220.

Furthermore, when three markers 15 are provided on the body section 14, the three markers 15 are arranged at vertices of a triangle having three sides of different lengths. Thereby, the orientation of the body section 14 can be uniquely specified by a relative positional relation of each of the markers 15. Each of the markers 15 is provided at a planar portion or a curved portion on the outer surface of the body section 14.

The marker 15 may be additionally provided on the body section 14 so as to be capable of specifying the position and orientation of the body section 14 even when a certain marker 15 is shielded with respect to the detection device 12 by obstacles or the like during manipulation. When a certain marker 15 is shielded, the position and orientation of the body section 14 are obtained alternatively using the additionally provided marker 15.

Moreover, three or more markers 15 may be disposed on one sheet and the sheet may also be attached to the outer surface of the body section 14.

Figure 3:
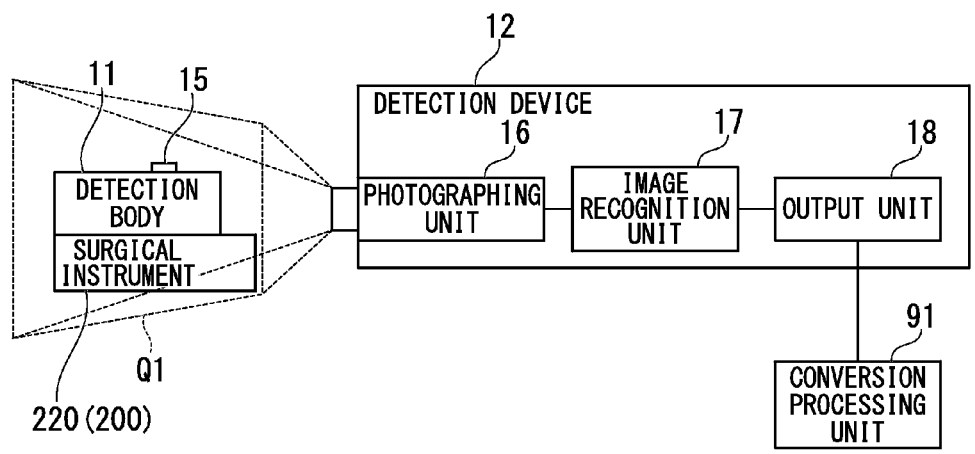
FIG. 3 is a block diagram of a detection device in the surgery assistance device according to the first embodiment of the present invention.

As shown in FIG. 3, the detection device 12 includes a photographing unit 16, an image recognition unit 17, and an output unit 18.

The photographing unit 16 is an apparatus configured to photograph the detection target object 11 when the surgical instrument 200 to which the detection target object 11 is attached is used by the user. A photographing field of vision of the photographing unit 16 is set to photograph an entire space (hereinafter referred to as "a working space Q1") in which the detection target object 11 is moved by the user upon use of the surgery assistance device 1. Although not shown in the drawings, the photographing unit 16 includes at least a first camera configured to photograph the working space Q1 from one predetermined direction, and a second camera configured to photograph the working space Q1 from a direction different from the predetermined one direction. Thereby, the photographing unit 16 can simultaneously photograph at least two images having different angles with respect to the detection target object 11 positioned in the working space Q1. The photographing unit 16 may also have three or more cameras. In addition, the photographing unit 16 may have configuration including a spare camera based on an assumption that a user themselves or another obstacle is interposed between the detection target object 11 and the camera. The photographing unit 16 outputs the photographed image to the image recognition unit 17.

The image recognition unit 17 recognizes the marker 15 from the photographed image through image recognition processing The image recognition unit 17 calculates a coordinate information as the position and orientation of the marker 15 from the positional relation of each marker 15 in the working space Q1, namely, first coordinate information A (detection target object information, see FIG. 2) which is coordinate information using a coordinate system intrinsic to the detection target object 11, and outputs the first coordinate information A to the output unit 18.

Since each marker 15 is provided on the body section 14 of the detection target object 11, the first coordinate information A serves as information which specifies the position and orientation of the detection target object 11.

The output unit 18 outputs the first coordinate information A calculated in the image recognition unit 17 to the conversion processing unit 91 of the control device 90 to be described later. In the embodiment, the first coordinate information A output from the output unit 18 is information for specifying the position and orientation of the detection target object 11 by the conversion processing unit 91. The first coordinate information A is output from the output unit 18 according to a predetermined transmission timing, regardless of whether or not the detection target object 11 moves in the working space Q1.

Figure 4:
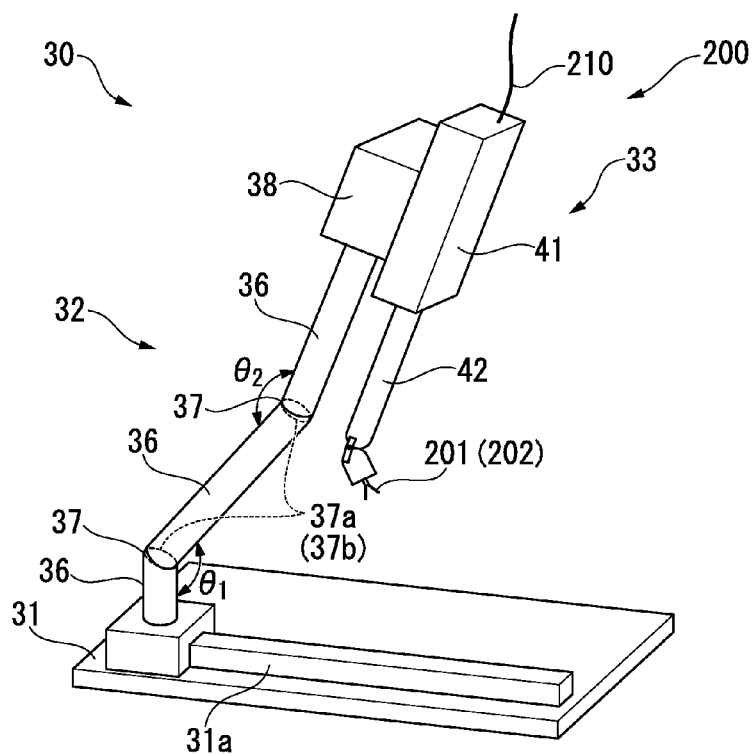
FIG. 4 is a perspective view schematically showing a slave manipulator of the surgery assistance device according to the first embodiment of the present invention.

As shown in FIG. 4, the slave manipulator 30 includes a holding manipulator 32 and a surgical instrument manipulator 33. The holding manipulator 32 is attached on a base 31. The surgical instrument manipulator 33 is detachably attached to the holding manipulator 32. In addition, the slave manipulator 30 includes a plurality of manipulators (holding manipulators 32 and surgical instrument manipulators 33), but only a set of manipulators 32 and 33 will be described below for the convenience of description.

The above surgical instrument 200 and an endoscopic device (not shown) (hereinafter referred to as "surgical instrument 200 and the like" in some cases) are attached to the slave manipulator 30.

In the holding manipulator 32, end portions of a plurality of rods 36 are rotatably interconnected through joint sections 37. A lower end portion of the holding manipulator 32 is slidably attached to a rail 31a provided on the base 31. A holding section 38 is fixed to a distal end of the holding manipulator 32, namely, to an end portion of the associated rod 36. A body section 41 of the surgical instrument manipulator 33 to be described later is detachably attached to the holding section 38 by an attachment and detachment mechanism (not shown). Each of the joint sections 37 is provided with an actuator 37a so that angles $\theta_1$ and $\theta_2$ formed by the adjacent rods 36 may be adjusted. The angles $\theta_1$ and $\theta_2$ formed by the rods 36 are detected by a joint angle detection sensor 37b such as an encoder provided in the joint section 37.

The endoscopic device provided in the slave manipulator 30 acquires images of a treatment object and the surgical instrument 200 and outputs these images to the display device 80.

Figure 5:
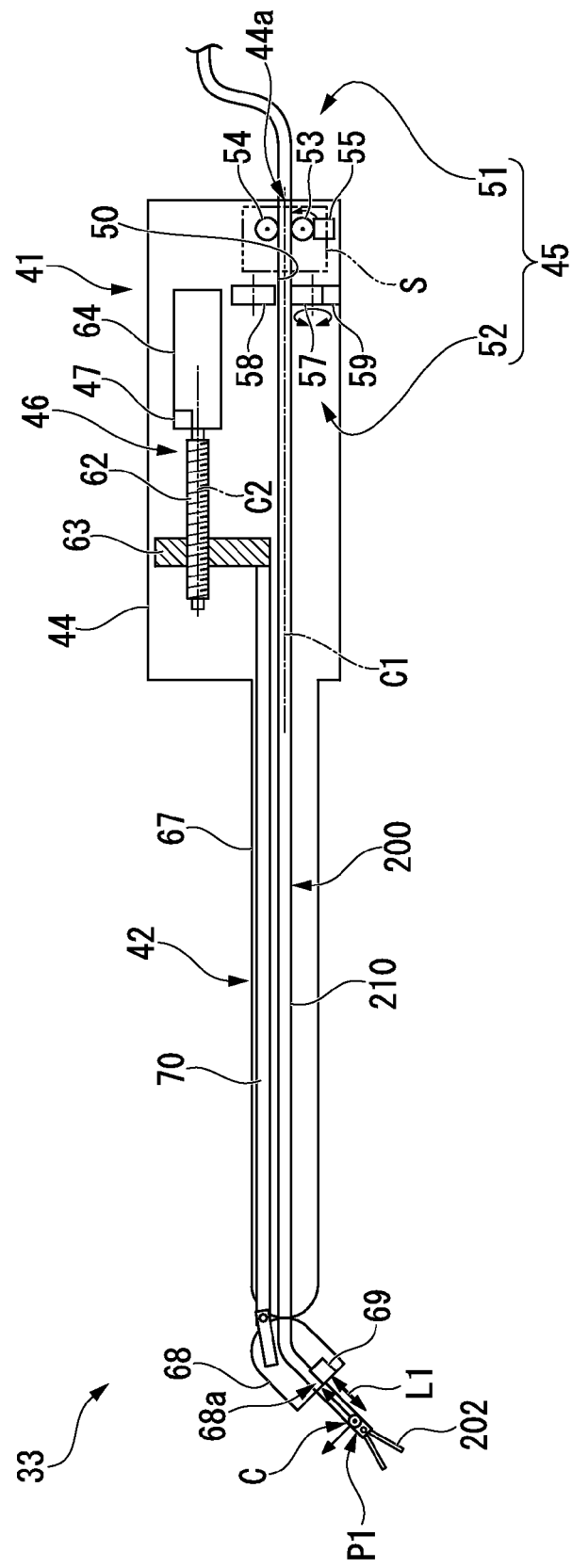
FIG. 5 is a cross-sectional view schematically showing main parts on the plane of a surgical instrument manipulator of the slave manipulator according to the first embodiment of the present invention.

As shown in FIGS. 4 and 5, the surgical instrument manipulator 33 includes a body section 41 and an insertion section 42. The insertion section 42 has a more elongated shape than the body section 41 and a proximal end portion of the insertion section 42 is connected to the body section 41.

As shown in FIG. 5, the body section 41 includes a casing 44, a movement amount detection means 45 accommodated in the casing 44, a swing mechanism 46, and a swing angle detection sensor 47.

A channel 50 is formed in the body section 41 and the insertion section 42 by a pipe material (not shown) or the like. The channel 50 communicates with a distal end opening 68a formed at a distal end side of the insertion section 42 and communicates with a proximal end opening 44a formed at the casing 44. In the channel 50, through-holes (not shown) are formed at portions provided with advancing/retracting rollers 53 and 54 and rotary rollers 57 and 58 to be described later, and the through-holes communicate with an inner space of the casing 44.

The above surgical instrument 200 may be inserted into the channel 50.

In the embodiment, the movement amount detection means 45 has an advancing/retracting movement amount detection section 51 and a rotary movement amount detection section 52.

The advancing/retracting movement amount detection section 51 has a pair of advancing/retracting rollers 53 and 54, and a length detection unit 55. The pair of advancing/retracting rollers 53 and 54 are arranged in the vicinity of the proximal end opening 44a such that the surgical instrument insertion section 210 of the surgical instrument 200 is interposed therebetween. The length detection unit 55 detects a rotation angle of the advancing/retracting roller 53. The advancing/retracting rollers 53 and 54 are disposed to rotate on a reference plane S including an axis C1 of the channel 50 and are supported by the casing 44. The length detection unit 55 has, for example, an encoder, a calculation element, and a memory. When the surgical instrument 200 advances and retracts with respect to the channel 50, the advancing/retracting rollers 53 and 54 rotate without slipping with respect to the surgical instrument insertion section 210 of the surgical instrument 200 and the rotation angle of the advancing/retracting roller 53 may be detected by the encoder.

The memory stores a length dimension of the surgical instrument 200 and the like. The calculation element may calculate a protrusion length by which the forceps 202 of the surgical instrument 200 inserted into the channel 50 protrudes forward from the distal end opening 68a of the channel 50, from the detected rotation angle of the advancing/retracting roller 53 and the length dimension of the surgical instrument 200 stored in the memory. In more detail, the calculation element may calculate a protrusion length L1 by which a connection position P1 between the forceps 202 and the surgical instrument insertion section 210 in the surgical instrument 200 protrudes forward from the distal end opening 68a.

The rotary movement amount detection section 52 has a pair of rotary rollers 57 and 58, and a rotation detection unit 59. The pair of rotary rollers 57 and 58 are disposed such that the surgical instrument insertion section 210 interposed therebetween. The rotation detection unit 59 detects a rotation angle of the rotary roller 57. The pair of rotary rollers 57 and 58 are supported by the casing 44 so as to be rotatable about an axis parallel with the axis C1. The rotation detection unit 59 has the same configuration as the length detection unit 55, and thus has an encoder, a calculation element, and a memory. When the surgical instrument 200 rotates about the axis C1, the rotary rollers 57 and 58 rotate without slipping with respect to the surgical instrument insertion section 210 of the surgical instrument 200 and the rotation angle of the rotary roller 57 may be detected by the encoder.

The memory stores a constant which expresses a ratio of an outer diameter of the rotary roller 57 to an outer diameter of the surgical instrument insertion section 210 and the like. The calculation element may calculate a rotation angle of the surgical instrument 200 about the axis C1 thereof, from the detected rotation angle of the rotary roller 57 and the constant stored in the memory.

These treatment section movement amounts which are the protrusion lengths and the rotation angles are output to an inverse kinematics computation unit 100 to be described later.

The swing mechanism 46 has a worm 62 and a worm wheel 63. The worm 62 is disposed so as to extend in parallel with the axis C1 of the channel 50. The worm wheel 63 engages with the worm 62. The worm 62 is rotatably supported by the casing 44. The worm wheel 63 is supported by the casing 44 so as to advance and retract.

A swing motor 64 is connected to a proximal end portion of the worm 62. The swing motor 64 is attached to the casing 44. The worm 62 rotates about an axis C2 parallel with the axis C1 of the channel 50 by the swing motor 64, thereby enabling the worm wheel 63 to be moved relative to the worm 62 in a direction of the axis C1.

The above swing angle detection sensor 47 is attached to the swing motor 64. The swing angle detection sensor 47 may properly select and use an encoder or the like. The swing angle detection sensor 47 may detect a rotation angle $\alpha$ of an axis of rotation of the swing motor 64, namely, a rotation angle of the worm 62 about the axis C2 thereof.

The insertion section 42 has an insertion section body 67 and a swing member 68. The insertion section body 67 has a tubular shape. The insertion section body 67 is fixed onto a distal end surface of the casing 44 and extends in the direction of the axis C1. The swing member 68 is swingably connected to a distal end portion of the insertion section body 67.

Although not shown in the drawings, one of the insertion section body 67 and the swing member 68 is provided with an axial member, and the other is formed with a hole which engages with the axial member so as to be relatively movable around the axial member. By such a configuration, the swing member 68 is swingably connected to the distal end portion of the insertion section body 67. The above distal end opening 68a is formed on the distal end surface of the swing member 68. The channel 50 communicates with the distal end opening 68a.

The swing member 68 is provided with a clip (fixing means) 69. The clip 69 fixes a position of the surgical instrument insertion section 210 inserted into the channel 50 with respect to the channel 50. In the embodiment, the clip 69 is provided at the distal end portion of the channel 50. By attaching the clip 69 to the surgical instrument insertion section 210, movement of the surgical instrument insertion section 210 in the direction of the axis C1 of the channel 50 with respect to the channel 50 and rotation of the surgical instrument insertion section 210 about the axis C1 with respect to the channel 50 are restricted.

A connecting rod 70 is inserted into a conduit of the insertion section body 67. A distal end portion of the connecting rod 70 is attached to the swing member 68 at a position shifted in a direction orthogonal to the axis C1 with respect to a swing center of the swing member 68 when viewed from the plane. A proximal end portion of the connecting rod 70 is attached to the worm wheel 63.

Therefore, the worm wheel 63 is moved in the direction of the axis C1 of the channel 50 by the swing motor 64, thereby enabling the swing member 68 to be swung relative to the insertion section body 67.

In the embodiment, the rod 36, the insertion section body 67, and the swing member 68 formed in a substantially tubular shape made of a material such as a metal are used. That is, each of the manipulators 32 and 33 is a so-called rigid manipulator.

Each actuator 37a provided in the holding manipulator 32 and the swing motor 64 provided in the surgical instrument manipulator 33 are actuated according to driving signals output from the control device 90. Thereby, it may be possible to move the channel 50 of the surgical instrument manipulator 33 with respect to the base 31 and to swing the swing member 68 of the surgical instrument manipulator 33.

Orientations of the holding manipulator 32 and surgical instrument manipulator 33 are uniquely specified based on the known kinematics from motion section information. The motion section information includes the angles $\theta_1$ and $\theta_2$ formed by the adjacent rods 36 detected by the joint angle detection sensor 37b and the rotation angle $\alpha$ of an axis of rotation of the swing motor 64 detected by the swing angle detection sensor 47. The position and orientation in the distal end of the slave manipulator 30, namely, the position and orientation in the distal end opening 68a of the swing member 68, may be specified. That is, the joint angle detection sensor 37b and the swing angle detection sensor 47 constitute a motion section information calculation means 48.

Furthermore, the position and orientation in the connection position P1 of the surgical instrument 200 may be specified based on the known kinematics using the rotation angle and protrusion length L1 of the above surgical instrument 200, in addition to the motion section information.

As shown in FIG. 1, the display device 80 is attached to the same base as the detection device 12 of the master manipulator 10 and is installed in the front of the user. The display device 80 has a display panel for displaying images acquired by the endoscopic device. A liquid crystal panel, an organic EL panel, or the like may be properly selected and adopted as the display panel.

Figure 6:
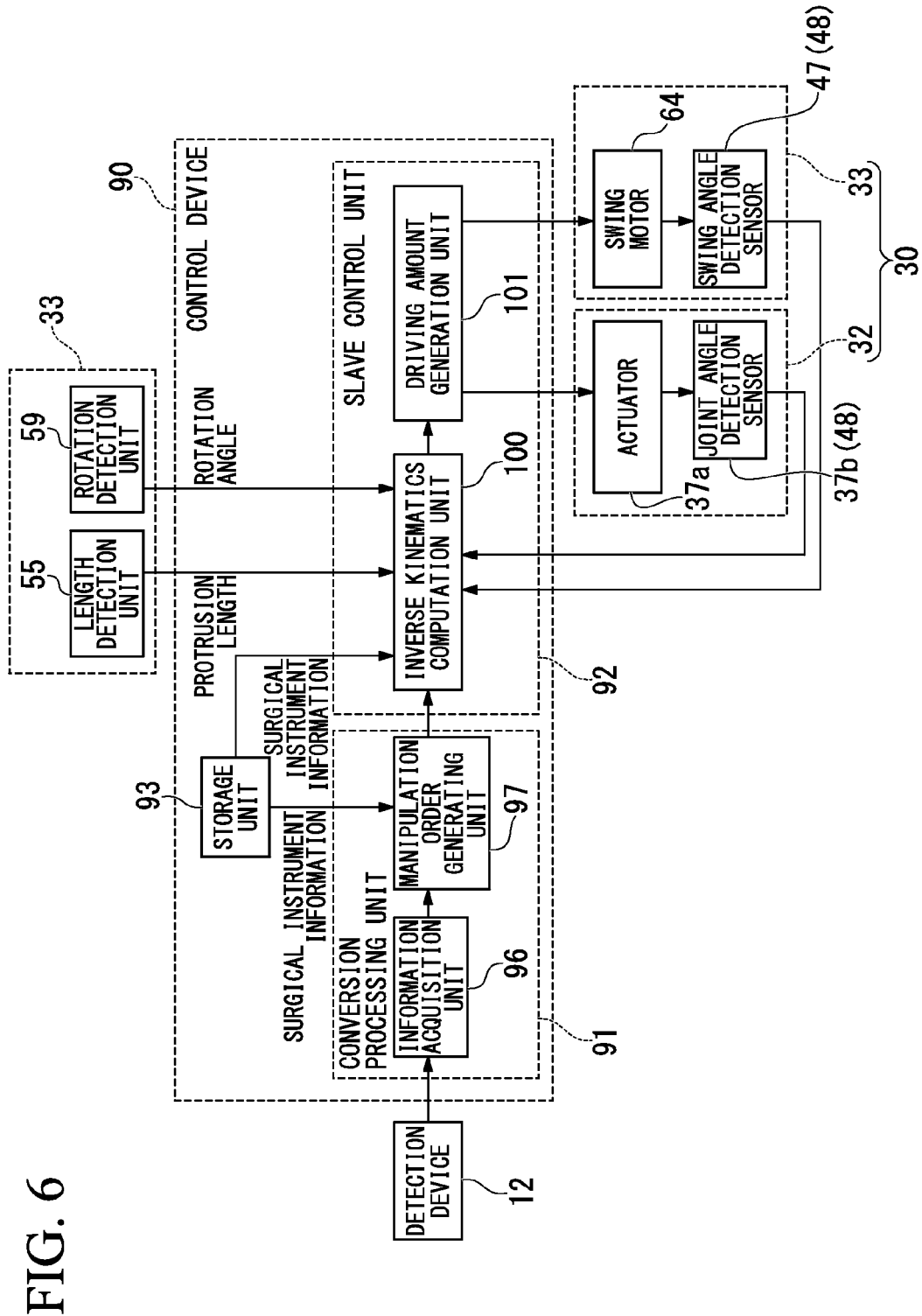
FIG. 6 is a block diagram of a control device and the slave manipulator in the surgery assistance device according to the first embodiment of the present invention.

As shown in FIGS. 1 and 6, the control device 90 includes a conversion processing unit 91, a slave control unit (motion control unit) 92, and a storage unit 93. The conversion processing unit 91 is connected to the detection device 12. The slave control unit 92 is connected to the conversion processing unit 91 and simultaneously connected to each actuator 37a of the slave manipulator 30 and the swing motor 64. The storage unit 93 is connected to the conversion processing unit 91 and the slave control unit 92.

The conversion processing unit 91 includes an information acquisition unit 96 and a manipulation order generation unit 97. The information acquisition unit 96 receives the first coordinate information A output from the detection device 12 shown in FIG. 3. The manipulation order generation unit 97 is connected to the information acquisition unit 96.

The information acquisition unit 96 acquires the first coordinate information A (see FIG. 1) calculated using the coordinate system intrinsic to the detection target object 11 and outputs the first coordinate information A to the manipulation order generation unit 97.

The first coordinate information A of the detection target object 11 output from detection device 12 shown in FIG. 3 is input to the manipulation order generation unit 97 via the information acquisition unit 96. The first coordinate information A of the detection target object 11 is input to the manipulation order generation unit 97 according to the above predetermined transmission timing. Subsequently, the first coordinate information A is acquired as tracking information of the detection target object 11 in the manipulation order generation unit 97.

The manipulation order generation unit 97 has a coordinate system conversion function. The coordinate system conversion function is a function for performing a process of converting a coordinate system of the tracking information of the detection target object 11 into a coordinate system of the operation section 220 to which the detection target object 11 is attached. The coordinate system of the operation section 220 is a coordinate system determined by the position of the marker 15 in the detection target object 11 and the shape of the operation section 220. In the embodiment, the coordinate system of the operation section 220 is a three-dimensional coordinate system which defines a connection position P2 (see FIG. 2) between the operation body 221 and the surgical instrument insertion section 210 as an original point. Information for specifying the coordinate system of the operation section 220 is stored as surgical instrument information in the storage unit 93 and is properly referred by the manipulation order generation unit 97. Thereby, the first coordinate information A in the tracking information of the detection target object 11 is converted into coordinate information (hereinafter referred to as "second coordinate information B", see FIG. 2) according to the three-dimensional coordinate system defining the connection position P2 as an original point.

For example, conversion of the coordinate system may be performed using a transformation matrix expressed by the following equation (1).

$$\{P_s\} = \{T\}\{P_m\} \qquad (1)$$

In the above equation (1), $\{P_m\}$ is a coordinate of the detection target object 11 based on the coordinate system intrinsic to the detection target object 11. $\{T\}$ is a known transformation matrix based on the surgical instrument information. $\{P_s\}$ is a coordinate of the operation section 220 defining the connection position P2 as an original point.

The manipulation order generation unit 97 outputs a manipulation order, which actuates the surgical instrument 200 and the slave manipulator 30 shown in FIG. 1, to the slave control unit 92. The manipulation order outputted by the manipulation order generation unit 97 includes, for example, the second coordinate information B which represents a position and an orientation after movement of the surgical instrument 200 and the slave manipulator 30 as an operation object.

The slave control unit 92 includes an inverse kinematics computation unit 100 and a driving amount generation unit 101. The inverse kinematics computation unit 100 is connected to the conversion processing unit 91. The driving amount generation unit 101 is connected to the inverse kinematics computation unit 100.

The inverse kinematics computation unit 100 acquires tracking information of the slave manipulator 30 from the joint angle detection sensor 37b provided in the holding manipulator 32 and the swing angle detection sensor 47 provided in the surgical instrument manipulator 33. The tracking information of the slave manipulator 30 is coordinate information (hereinafter referred to as "third coordinate information C") in the three-dimensional coordinate system which represents the positions and orientations of the surgical instrument 200 and slave manipulator 30 and the position and orientation of the treatment section 201 (connection position P1) provided in the surgical instrument 200. That is, an original point in the third coordinate information C is the connection position P1 in a state in which the surgical instrument 200 is inserted into the channel 50 of the surgical instrument manipulator 33 to be fixed by the clip 69. The third coordinate information C is obtained in consideration of the angles $\theta_1$ and $\theta_2$ formed by the rods 36, the rotation angle $\alpha$ of the swing motor 64, and the protrusion length L1 and rotation angle of the connection position P1.

The inverse kinematics computation unit 100 converts manipulation orders output from the conversion processing unit 91 into the rotation angle $\alpha$ of the swing motor 64 and the angles $\theta_1$ and $\theta_2$ formed by the rods 36 in each joint section 37 of the slave manipulator 30, in response to the manipulation orders from the manipulation order generation unit 97, and outputs the converted data to the driving amount generation unit 101.

The inverse kinematics computation unit 100 may also have a coordinate conversion function, if necessary. The coordinate conversion function is a function for matching the coordinate system of the second coordinate information B with the coordinate system of the third coordinate information C by coordinate conversion. When the coordinate system of the second coordinate information B and the coordinate system of the third coordinate information C are matched by coordinate conversion, the user moving the treatment section 201 by viewing images of the endoscope may intuitively move the treatment section 201.

The inverse kinematics computation unit 100 may also have a scale conversion function. The scale conversion function matches a scale in the tracking information of the detection target object 11 with a scale in the tracking information of the slave manipulator 30.

The operation of the user moving the detection target object 11 while viewing the display device 80 may be reflected in the operations of the slave manipulator 30 and surgical instrument 200 by the coordinate conversion function and the scale conversion function.

The driving amount generation unit 101 outputs a driving signal to each actuator 37a and the swing motor 64, and controls motion of the slave manipulator 30. The driving signal is a signal for defining driving amounts of each actuator 37a and the swing motor 64 corresponding to movement angles output from the inverse kinematics computation unit 100.

Next, the motion and operation during the use of the surgery assistance device 1 according to the embodiment will be described. Hereinafter, an example will be described in which the treatment section 201 is moved by operating the operation section 220 such that the position and orientation with respect to the connection position P2 of the operation section 220 and the position and orientation with respect to the connection position P1 of the treatment section 201 have a correlation.

Figure 7:
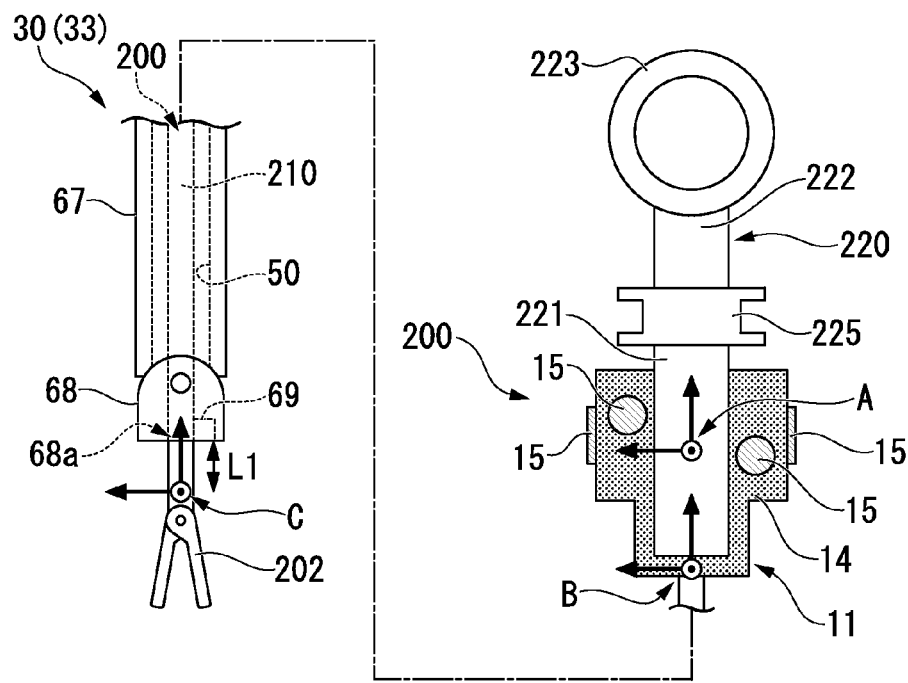
FIG. 7 is a schematic view showing a motion during use of the surgery assistance device according to the first embodiment of the present invention.

When the surgery assistance device 1 is used, the user inserts the surgical instrument 200 into the channel 50 of the slave manipulator 30, as shown in FIG. 7. In this case, the forceps 202 protrudes from the distal end opening 68a of the channel 50.

By advancing, retracting, and twisting of the surgical instrument 200 with respect to the channel 50, the position and direction of the forceps 202 are adjusted with respect to the distal end opening 68a. The protrusion length L1 caused by advancing and retracting the surgical instrument 200 by the user is detected by the length detection unit 55. The rotation angle of the surgical instrument 200 twisted by the user is detected by the rotation detection unit 59.

The position at the distal end side of the surgical instrument insertion section 210 with respect to the channel 50 is fixed by the clip 69.

The detected protrusion length L1 and rotation angle are output to the inverse kinematics computation unit 100. Here, the protrusion length L1 and rotation angle after fixing the position of the surgical instrument insertion section 210 with respect to the channel 50 by the clip 69 become constant values.

Hereinafter, a case in which a protrusion length L1 is set to be relatively short will be first described.

Figure 8:
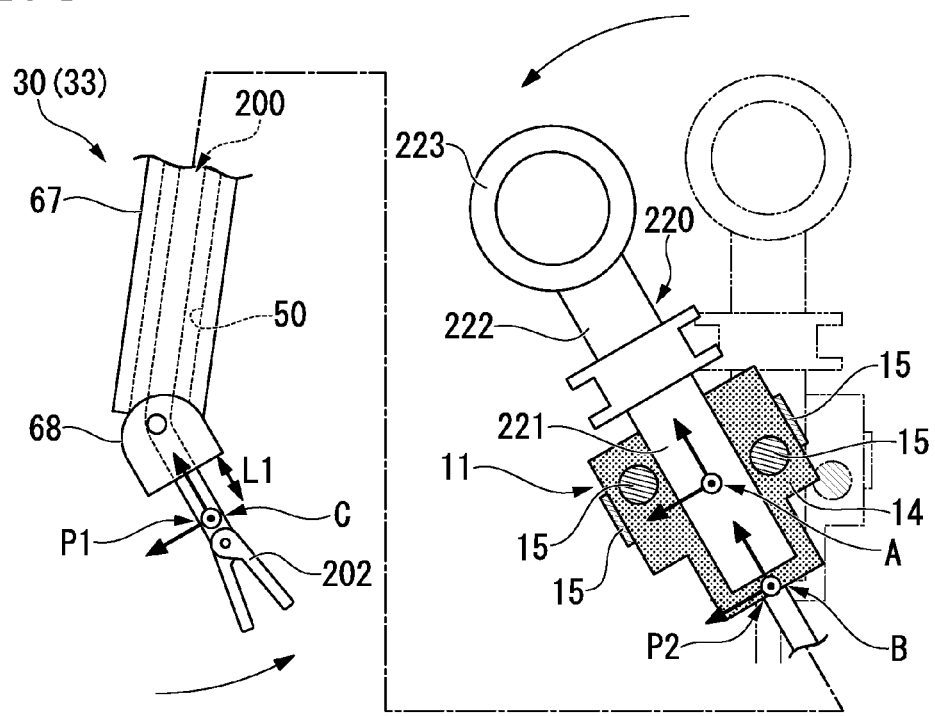
FIG. 8 is a schematic view showing a motion when a protrusion length is relatively short during the use of the surgery assistance device according to the first embodiment of the present invention.

When the surgical instrument 200 is used, the operation section 220 of the surgical instrument 200 is gripped by the user and the operation section 220 is moved if necessary, as shown in FIG. 8. Thereby, the detection target object 11 attached to the operation section 220 is also moved together with the operation section 220 and the marker 15 provided on the detection target object 11 is moved in the working space Q1. In this case, the marker 15 is photographed by the photographing unit 16 provided in the detection device 12 shown in FIG. 3.

The detection device 12 detects the position and orientation of the marker 15 in the working space Q1 and outputs the first coordinate information A to the conversion processing unit 91 of the control device 90.

In the conversion processing unit 91, the manipulation order (see FIG. 1) including the second coordinate information B formed by coordinate conversion of the first coordinate information A is generated based on the first coordinate information A (tracking information of the detection target object 11) by the manipulation order generation unit 97. The manipulation order generated by the manipulation order generation unit 97 is output to the inverse kinematics computation unit 100 of the slave control unit 92.

In the inverse kinematics computation unit 100, the second coordinate information B included in the manipulation order is compared to the tracking information (third coordinate information C) of the slave manipulator 30 acquired from the slave manipulator 30. Using this comparative result, the inverse kinematics computation unit 100 calculates the angles $\theta_1$ and $\theta_2$ formed by the respective rods 36 for controlling the position and orientation of the holding manipulator 32 and the rotation angle $\alpha$ of the swing motor 64 for controlling the position and orientation of the surgical instrument manipulator 33. The inverse kinematics computation unit 100 outputs the calculated angles $\theta_1$ and $\theta_2$ and rotation angle $\alpha$ to the driving amount generation unit 101.

The driving amount generation unit 101 generates driving signals for defining the driving amounts of the actuator 37a of the slave manipulator 30 and the swing motor 64 according to the movement angles output from the inverse kinematics computation unit 100, and moves the slave manipulator 30 and the surgical instrument 200.

Accordingly, for example, when the user operates such that the orientation of the operation section 220 is changed by rotating the operation section 220 about the connection position P2 of the operation section 220 as a center of rotation as shown in FIG. 8, this is controlled by the control device 90 as follows. That is, by adjusting the angles $\theta_1$ and $\theta_2$ formed by the respective rods 36 and the rotation angle $\alpha$ of the swing motor 64, the surgical instrument 200 is moved such that the orientation of the operation section 220 coincides with the orientation of the forceps 202 without movement of the connection position P1 of the treatment section 201 in the space.

Figure 9:
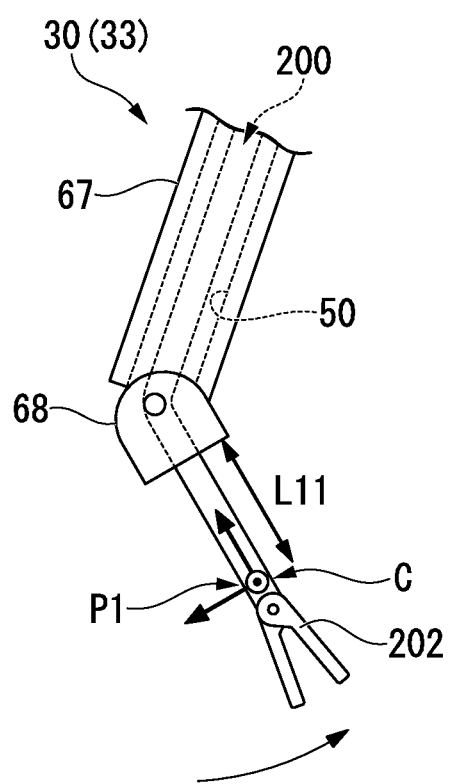
FIG. 9 is a schematic view showing a motion when a protrusion length is relatively long during the use of the surgery assistance device according to the first embodiment of the present invention.

Here, a case in which a protrusion length L11 is set to be relatively long will be first described as shown in FIG. 9.

In this case, the protrusion length L11 is longer than the above protrusion length L1. For this reason, the protrusion length L11 is output to the inverse kinematics computation unit 100, thereby allowing the angles $\theta_1$ and $\theta_2$ formed by the respective rods 36 and the rotation angle $\alpha$ of the swing motor 64 to be recalculated. Since each rod 36 and the swing member 68 are largely moved compared to FIG. 8, the surgical instrument 200 is moved without movement of the connection position P1.

In the embodiment, since the position and orientation of the forceps 202 are controlled as described above, the user can obtain an operational feeling as if the forceps 202 were fixed to the connection position P2. That is, the user operating the operation section 220 in the embodiment may use the surgical instrument 200 with an operational feeling as if he or she were using a rigid instrument in which the forceps pieces 202a and 202b are attached to the connection position P2 of the operation body 221.

Next, a case in which the forceps pieces 202a and 202b are openably and closably operated will be described.

By advancing and retracting the slider 225 with respect to the operation body 221, the wire 204 advances and retracts in the surgical instrument insertion section 210 and the forceps pieces 202a and 202b are opened and closed. A touch felt when tissue or the like is grasped by the pair of forceps pieces 202a and 202b is transferred to the slider 225 via the wire 204, and the touch is transferred as an operational feeling to the user operating the slider 225.

When the protrusion length and rotation angle of the surgical instrument 200 are adjusted, the position of the forceps 202 is adjusted by advancing, retracting, and twisting of the surgical instrument 200 by removal of the clip 69 from the surgical instrument insertion section 210. Subsequently, the clip 69 is attached to the surgical instrument insertion section 210. In this case, the protrusion length and rotation angle of the surgical instrument 200 are detected again by the movement amount detection means 45 and output to the inverse kinematics computation unit 100.

As described above, in accordance with the surgery assistance device 1 according to the embodiment, the protrusion length L1 and rotation angle of the surgical instrument 200 are detected by the movement amount detection means 45. These detected values are output to the inverse kinematics computation unit 100 so that the angles $\theta_1$ and $\theta_2$ formed by the respective rods 36 and the rotation angle $\alpha$ of the swing motor 64 are calculated and the slave manipulator 30 is driven. Therefore, even when the protrusion length L1 and rotation angle of the surgical instrument 200 are changed, the position and orientation of the operation section 220 to which the detection target object 11 is attached may coincide with the position and orientation of the forceps 202. As a result, the user may intuitively operate the flexible surgical instrument 200.

In accordance with the surgery assistance device 1 according to the embodiment, since the clip 69 is provided in the swing member 68, the protrusion length L1 of the surgical instrument 200 protruding from the distal end opening 68a and the rotation angle of the surgical instrument 200 are possible to be fixed and the treatment is possible to be performed while stabilizing the surgical instrument 200.

The detection target object 11 has the marker 15 provided in the body section 14, and the detection device 12 calculates the first coordinate information A using the marker 15. Consequently, the first coordinate information A of the detection target object 11 may be calculated by a relatively simple configuration.

In the embodiment, the case in which the protrusion length of the surgical instrument 200 is changed has been exemplarily described. Furthermore, even when the rotation angle of the surgical instrument 200 is changed, the angles $\theta_1$ and $\theta_2$ formed by the respective rods 36 and the rotation angle $\alpha$ of the swing motor 64 may be adjusted such that the position and orientation of the operation section 220 to which the detection target object 11 is attached coincide with the position and orientation of the forceps 202. As a result, the user may intuitively operate the surgical instrument 200.

(Second Embodiment)

Next, a second embodiment of the present invention will be described with reference to FIGS. 10 and 11. The same elements as in the above-mentioned embodiment are designated by like reference numerals and a description thereof will be omitted. In addition, only different elements will be described.

Figure 10:
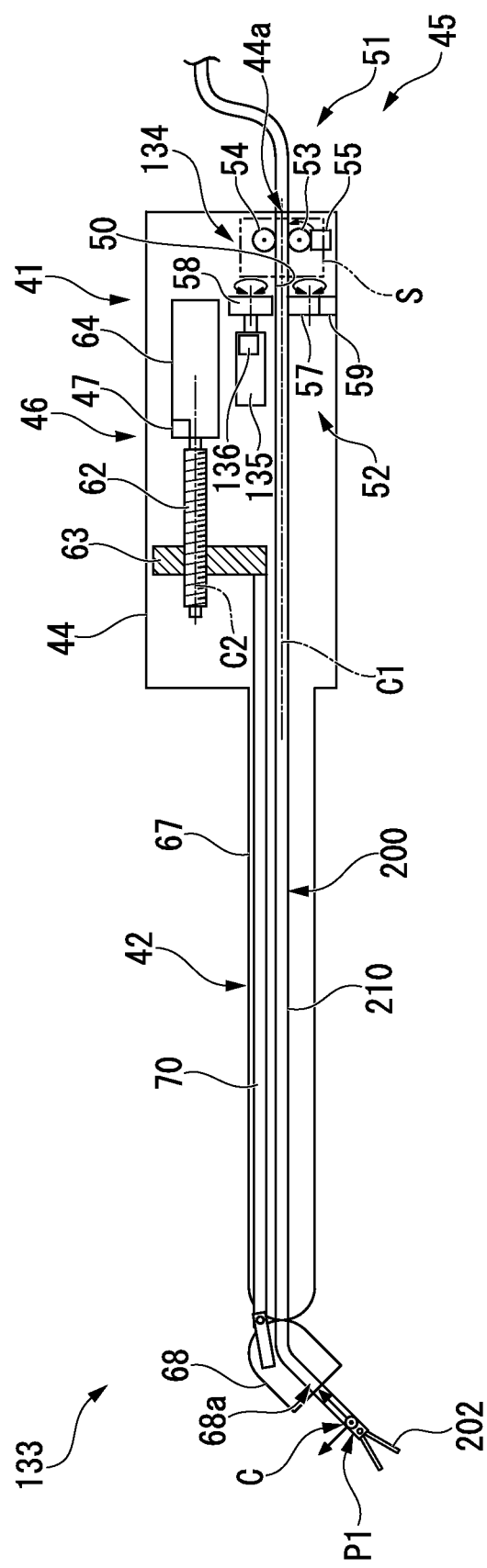
FIG. 10 is a cross-sectional view schematically showing main parts on the plane of a surgical instrument manipulator in the surgery assistance device according to the second embodiment of the present invention.

As shown in FIG. 10, a surgical instrument manipulator 133 in the surgery assistance device according to the embodiment includes a surgical instrument movement section 134 which rotates the surgical instrument 200 inserted in the channel 50 about the axis C1 of the channel 50, in place of the clip 69 with respect to the surgical instrument movement section 33 according to the first embodiment.

Figure 11:
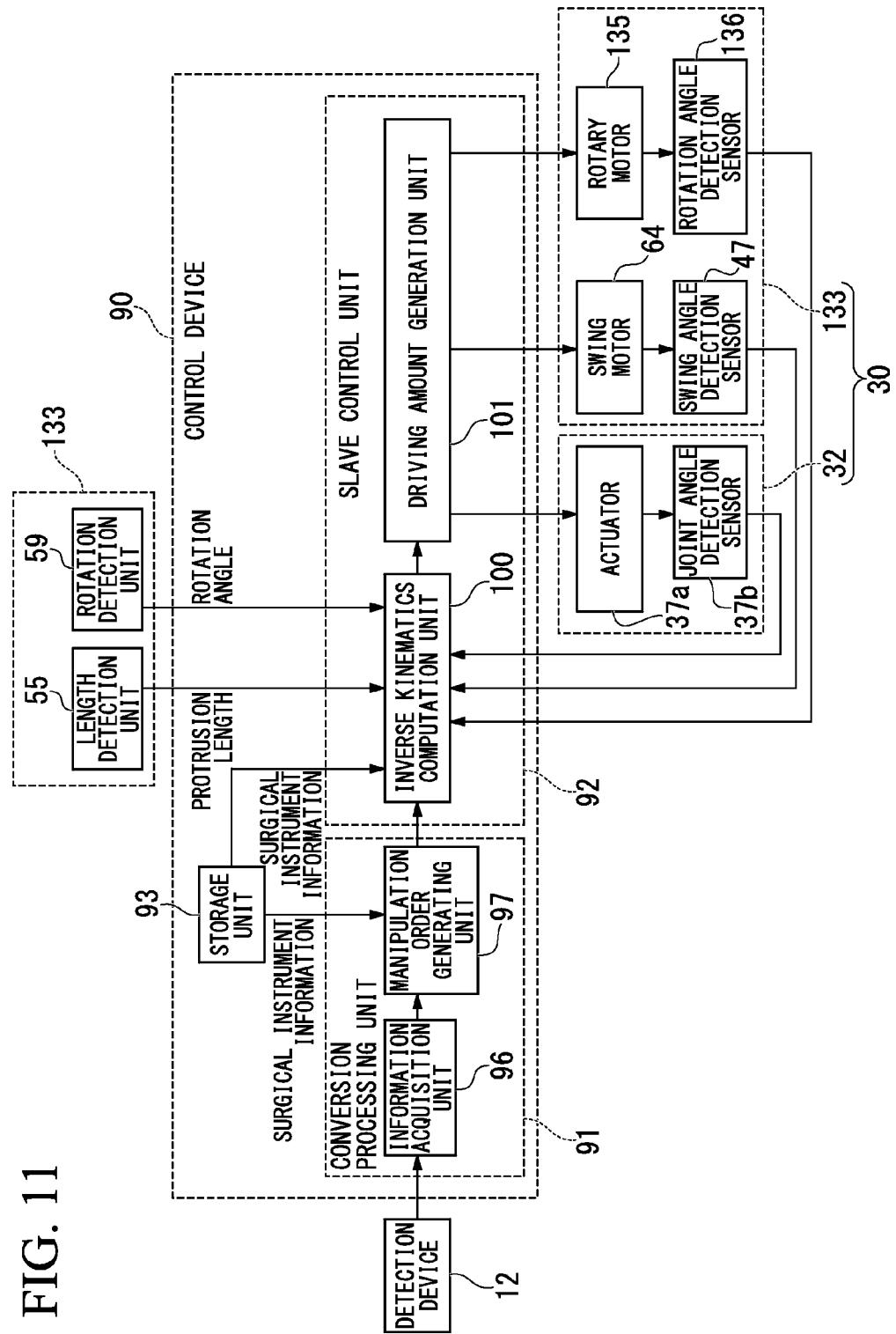
FIG. 11 is a block diagram of a control device and a slave manipulator in the surgery assistance device according to the second embodiment of the present invention.

As shown in FIGS. 10 and 11, the surgical instrument movement section 134 has the above-mentioned rotary roller 58, a rotary motor 135, and a rotation angle detection sensor 136. The rotary motor 135 rotates the rotary roller 58 about the axis thereof. The rotation angle detection sensor 136 detects a rotation angle of an axis of rotation of the rotary motor 135.

The rotary motor 135 is rotatably supported by the casing 44. The rotation angle detection sensor 136 may properly use an encoder or the like.

The rotation angle detection sensor 136 is connected to the inverse kinematics computation unit 100 and outputs the detected result of the rotation angle of the rotary motor 135 to the inverse kinematics computation unit 100.

In accordance with the surgery assistance device according to the embodiment having such a configuration, even when the protrusion length and rotation angle of the surgical instrument 200 are changed, the forceps 202 may be intuitively operated.

Since the clip 69 is not provided, the rotation angle of the surgical instrument 200 may be adjusted by moving the surgical instrument 200 with respect to the channel 50 by the surgical instrument movement section 134 even during the procedure. Therefore, an intuitive operation may continue without stopping the procedure. In addition, it may be possible to enhance the degree of freedom in rotating the surgical instrument 200 about the axis C1.

Although the embodiment has been described as an example in which the surgical instrument movement section 134 is a mechanism rotating the surgical instrument 200 about the axis C1, the present invention is not limited thereto. For example, a surgical instrument movement section may be used a mechanism in which the surgical instrument 200 is capable of advancing and retracting in the channel 50 in the direction of the axis C1. A surgical instrument movement section may also be used a mechanism in which the surgical instrument 200 rotates about the axis C1 and simultaneously advances and retracts in the direction of the axis C1.

(Third Embodiment)

Next, a third embodiment of the present invention will be described with reference to FIG. 12. The same elements as in the above-mentioned embodiments are designated by like reference numerals and description thereof will be omitted. In addition, only different elements will be described.

Figure 12:
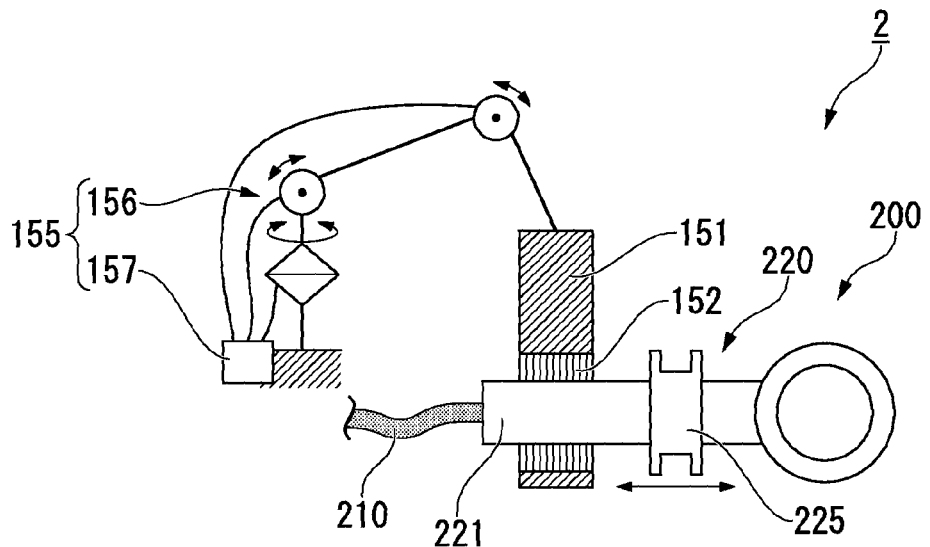
FIG. 12 is a schematic view showing main parts in the surgery assistance device according to the third embodiment of the present invention.

As shown in FIG. 12, a surgery assistance device 2 according to the embodiment has an adaptor 151 attached to the operation section 220, in place of the detection target object 11 having the marker 15 according to the first embodiment.

The adaptor 151 and the operation section 220 are interconnected through an annular member (intermediate member) 152.

In addition, the surgery assistance device 2 includes a detection device 155 including an articulated arm 156 and a position-orientation detection section 157, in place of the detection device 12 including the photographing unit 16 and the image recognition unit 17. The articulated arm 156 is connected to the adaptor 151. The position-orientation detection section 157 detects a position and orientation of the articulated arm 156.

The position-orientation detection section 157 includes angle detectors such as an encoder which detects a movement angle of each joint of the articulated arm 156. The position-orientation detection section 157 acquires the above-mentioned first coordinate information (detection target object information) based on information of an angle output from each angle detector.

In addition, the detection device 155 has the same output section as the output unit 18 according to the first embodiment, and tracking information of the adaptor 151 may be output to the conversion processing unit 91 through the output section.

The adaptor 151 and the position and orientation of the operation section 220 connected to the adaptor 151 are specified using the articulated arm 156 in the embodiment, in place of detecting the marker 15 in the working space Q1 in the first embodiment (see FIG. 3).

The surgery assistance device 2 according to the embodiment having such a configuration may also achieve the same effect as the surgery assistance device 1 according to the first embodiment.

In addition, in the embodiment, a case in which the marker 15 is blocked by obstacles and photographing of the marker 15 by the photographing unit 16 is disturbed may not be generated. Therefore, the tracking information of the adaptor 151 may be reliably obtained.

Although the first to third embodiments of the present invention have been described with reference to the drawings, the specific configuration is not limited thereto.

Figure 13:
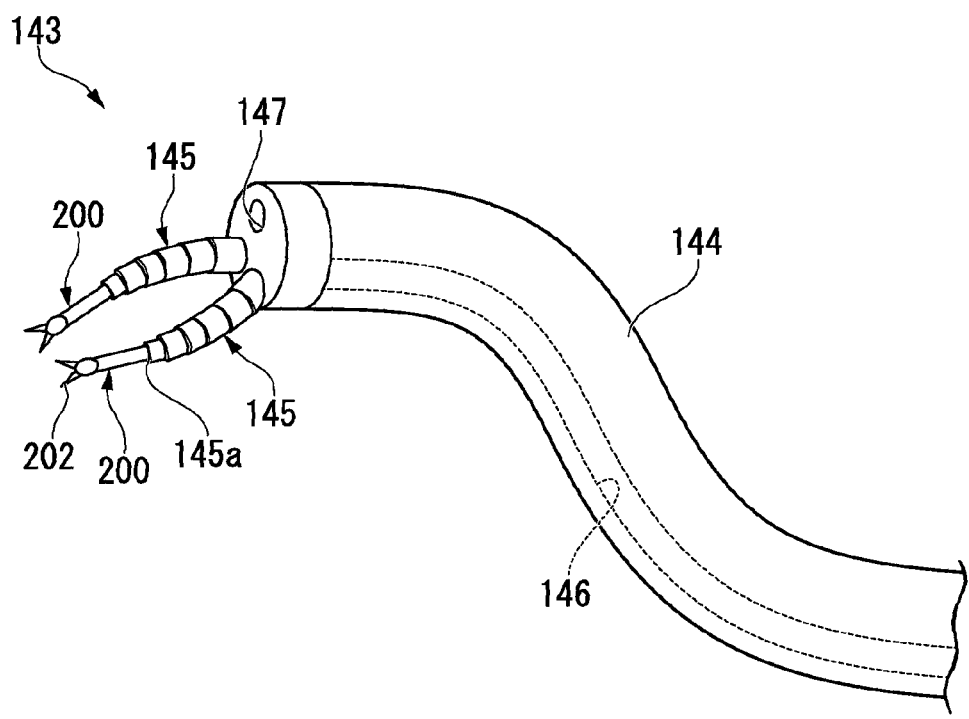
FIG. 13 is a perspective view schematically showing a surgical instrument manipulator in the surgery assistance device according to a modified embodiment of the present invention.

For example, in the first to third embodiments, the manipulator has rigidity. Furthermore, as shown in a modified example of FIG. 13, a so-called flexible manipulator may also be used as a surgical instrument manipulator 143.

In the modified example, an insertion section body 144 is made of a flexible material such as a resin. A pair of distal end joint sections 145 is provided on a distal end surface of the insertion section body 144. A channel 146 is formed in the distal end joint sections 145 and the insertion section body 144. The channel 146 communicates with a distal end opening 145a formed at the distal end of each distal end joint section 145.

The distal end surface of the insertion section body 144 is provided with an observation unit 147 having an imaging element such as a CCD in a state in which the observation unit 147 is exposed. The surgical instrument manipulator 143 is used as an endoscope.

Thus, even when the surgical instrument manipulator 143 is configured to have rigidity, a protrusion length of the surgical instrument 200 protruding from the distal end opening 145a inserted into the channel 146 is detected and motion of the distal end joint section 145 is controlled such that a position and orientation on the screen of the endoscope coincide with the position and orientation of the operation section 220. Thus, the embodiment may obtain the same effect as that of the first embodiment.

In the first to third embodiments, the movement amount detection means 45 detects both of the protrusion length and the rotation angle as the treatment section movement amounts. Furthermore, the movement amount detection means 45 may also be configured to detect one of the protrusion length and the rotation angle. For example, when a surgical instrument such as a local injection needle which is rotationally symmetric about an axis is used, the rotation angle of the surgical instrument may not be detected either.

Although embodiments have been described with reference to a number of illustrative embodiments thereof, it should be understood that numerous other modifications and applications may be devised by those skilled in the art that will fall within the intrinsic aspects of the embodiments. More particularly, various variations and modifications are possible in concrete constituent elements of the embodiments. In addition, it is to be understood that differences relevant to the variations and modifications fall within the spirit and scope of the present disclosure defined in the appended claims.

What is claimed is:

1. A surgery assistance device comprising:
   an operation input section configured to output a manipulation order based on input from a user;
   a motion section which is formed with a channel into which a surgical instrument is insertable and is capable of moving in the channel, the surgical instrument provided with a treatment section at a distal end portion of a flexible surgical instrument insertion section;
   a movement amount detection means detecting a treatment section movement amount which is a protrusion length by which the treatment section of the surgical instrument inserted into the channel protrudes forward from a distal end opening of the channel and a rotation angle of the surgical instrument about an axis of the channel;
   a motion section information calculation means calculating motion section information which is capable of specifying a position and an orientation of the surgical instrument in the distal end opening of the channel; and
   a motion control unit controlling motion in the motion section based on the manipulation order,
   wherein the operation input section comprises:
   a detection target object attached to an operation section which operates the treatment section fixed to a proximal end portion of the surgical instrument insertion section; and
   a detection section detecting the detection target object,
   wherein the detection section calculates detection target object information capable of specifying a position and orientation of the detection target object,
   the operation input section outputs the manipulation order based on the detection target object information calculated by the detection section, and
   the motion control unit controls motion in the motion section based on the detection target object information of the manipulation order, the treatment section movement amount, and the motion section information.

2. The surgery assistance device according to claim 1, further comprising a fixing means configured to fix a position of the surgical instrument insertion section inserted into the channel with respect to the channel.

3. The surgery assistance device according to claim 1, further comprising a surgical instrument movement section moving the surgical instrument inserted into the channel with respect to the channel.

4. The surgery assistance device according to claim 1,
   wherein the detection target object comprises:
   a body section attached to the operation section; and
   a marker provided at the body section, and
   the detection section calculates the detection target object information using the marker.

5. The surgery assistance device according to claim 4,
   wherein the detection section calculates the detection target object information by using a coordinate system defining an original point, which is set to have a predetermined positional relation with respect to the operation section, as a reference.

6. The surgery assistance device according to claim 1, wherein the detection target object comprises an adaptor attached to the operation section, and the detection section comprises:

an articulated arm connected to the adaptor; and a position-orientation detection section detecting a position and orientation of the articulated arm to output the position and orientation as the detection target object information.

7. The surgery assistance device according to claim 6, wherein the detection section calculates the detection target object information by using a coordinate system defining an original point, which is set to have a predetermined positional relation with respect to the operation section, as a reference.

8. The surgery assistance device according to claim 1, wherein the movement amount detection means detects a rotation amount of the surgical instrument insertion section to detect the rotation angle of the surgical instrument.

9. The surgery assistance device according to claim 1, wherein the movement amount detection means comprises:

a rotary roller rotating in accordance with a rotation of the surgical instrument insertion section; and a rotation detection unit detecting a rotation angle of the rotary roller.

* * * * *